United States Patent [19]

Mesek et al.

[11] 4,102,340
[45] Jul. 25, 1978

[54] DISPOSABLE ARTICLE WITH PARTICULATE HYDROPHILIC POLYMER IN AN ABSORBENT BED

[75] Inventors: Frederick K. Mesek, Downers Grove; Virginia L. Repke, Oak Forest, both of Ill.

[73] Assignee: Johnson & Johnson, New Brunswick, N.J.

[21] Appl. No.: 795,149

[22] Filed: May 9, 1977

Related U.S. Application Data

[63] Continuation of Ser. No. 531,130, Dec. 9, 1974, abandoned.

[51] Int. Cl.² ............................................. A61F 13/16
[52] U.S. Cl. .................................................. 128/287
[58] Field of Search .............. 128/284, 285, 286, 287, 128/290 R, 291,; 154/54

[56] References Cited

U.S. PATENT DOCUMENTS

| | | |
|---|---|---|
| 3,528,421 | 9/1970 | Vaillancourt et al. ............... 128/287 |
| 3,858,585 | 1/1975 | Chatterjee ....................... 128/290 R |
| 3,888,257 | 6/1975 | Cook et al. ......................... 128/296 |
| 3,916,900 | 11/1975 | Breyer et al. ........................ 128/287 |

*Primary Examiner*—Kyle L. Howell
*Assistant Examiner*—V. Millin

[57] ABSTRACT

An absorbent article such as a diaper or a sanitary napkin is made up of a facing sheet, an absorbent pad means, and a moisture-impervious backing sheet. The absorbent pad means comprises a fibrous structure having an intermediate densified layer and a layer of highly porous, loosely compacted batt on both sides of the densified layer. The batt layer between the densified fibrous layer and the moisture-impervious backing sheet contains distributed therein a particulate, water-insoluble but water-swellable polymeric absorbent.

25 Claims, 7 Drawing Figures

U.S. Patent     July 25, 1978     4,102,340
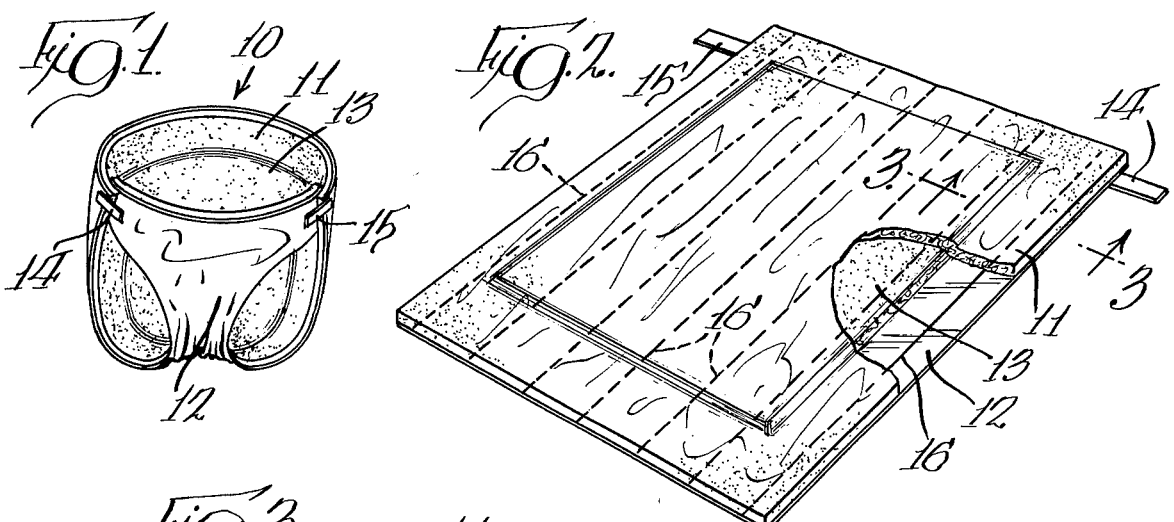
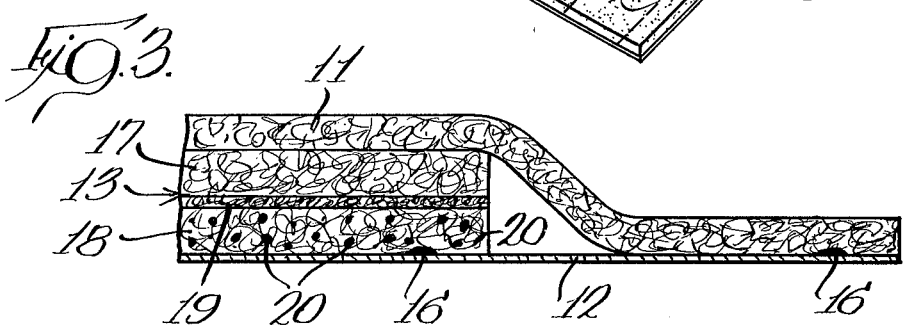
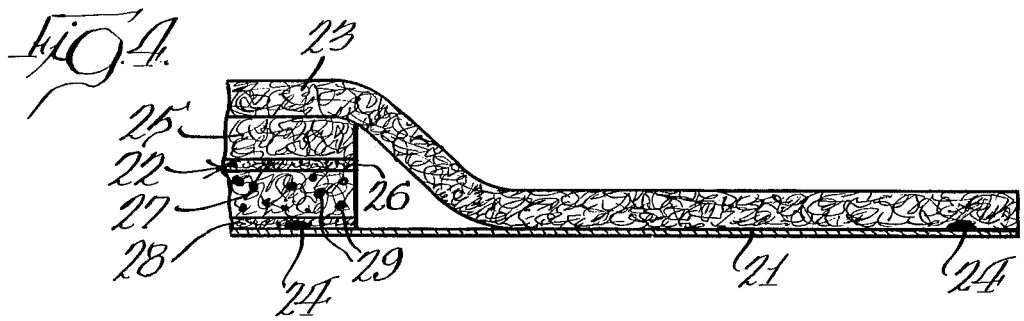
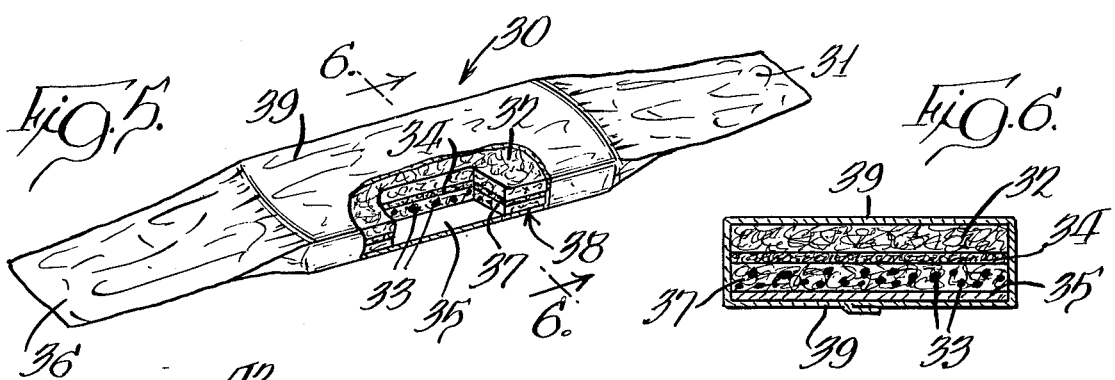
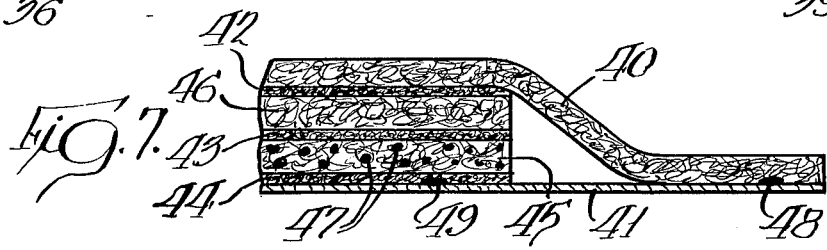

DISPOSABLE ARTICLE WITH PARTICULATE HYDROPHILIC POLYMER IN AN ABSORBENT BED

This is a continuation of application Ser. No. 531,130 filed Dec. 9, 1974, now abandoned.

BACKGROUND OF THE INVENTION

This invention relates to disposable absorbent articles such as disposable diapers, sanitary napkins, and the like.

Disposable diapers provide substantial advantages in convenience over diapers that have to be laundered and reused, particularly when the diapers are used away from home. In recent years, many different disposable diapers have been proposed and some have been successful in the marketplace. However, even the successful diapers are inadequate in functioning properties, and their commercial success has come because consumers have been willing to accept inadequate performance as part of the price for convenience.

One design criterion which has not heretofore been met adequately is keeping moisture away from the surface of the diaper which comes into contact with the infant's skin to thereby avoid skin irritation and infection.

Another important criterion is ready conformability to the body of the infant for maximum comfort.

In one form of prior disposable diaper, creped cellulose wadding is used as the absorbent material, covered with a permeable paper-like facing material on the side to be brought into contact with the infant's skin and covered with an impervious plastic sheet on the outside. In such a diaper, the wadding becomes more or less uniformly saturated with urine as the infant voids and thus a substantial amount of moisture is only a paper's thickness away from the infant's skin. In use, the weight of the infant presses the paper-like facing layer against the saturated wadding so that substantial amounts of moisture are expressed form the diaper and pass through the facing and into contact with the infant's skin.

Finally, both the paper-like facing material and the creped wadding of this prior art diaper are relatively stiff, making for an uncomfortable diaper, particularly when sufficient wadding is present to absorb a reasonable amount of urine.

It is also known to incorporate water-insoluble but absorbent particulate matter into the absorbent region of the disposable absorbent articles. Such particulate matter is disclosed in U.S. Pat. No. 3,669,103 to Harper et al., U.S. Pat. No. 3,670,731 to Harmon, and U.S. Pat. No. 3,783,872 to King. However, such particulate matter tends to swell and form a gelatinous layer which, while quite absorbent, tends to block liquid passage therethrough. As a result the full absorptive capacity of the absorbent article of manufacture is not utilized because the liquid to be absorbed cannot reach the absorbent material.

SUMMARY OF THE INVENTION

The present invention provides an absorbent article which can be applied to an animal body, which permits an improved utilization of substantially all absorbent material therewithin, and which possesses a relatively high overall absorptive capacity for body liquids.

According to the present invention, an absorbent article is made up of an absorbent pad means, a moisture-impervious backing sheet for the pad means, and a facing sheet which overlies the pad means. The pad means comprises a fibrous structure having an intermediate densified layer, a layer of highly porous, loosely-compacted batt on both sides of the densified layer, and a particulate, water-insoluble but water-swellable polymeric absorbent distributed in the batt layer between the densified layer and the moisture-impervious backing sheet. A further densified layer can be provided between the particulate absorbent-bearing batt layer and the backing sheet, and/or immediately adjacent to the facing sheet, if desired.

BRIEF DESCRIPTION OF THE DRAWINGS

In the drawings,

FIG. 1 is a perspective view of a disposable diaper embodying the present invention in a configuration assumed by the diaper when placed about an infant;

FIG. 2 is a perspective view of an open, unfolded diaper in accordance with one embodiment of this invention, parts of the diaper being broken away to show interior detail;

FIG. 3 is a partial sectional elevation taken along plane 3—3 in FIG. 2;

FIG. 4 is a partial sectional elevation similar to FIG. 3 and showing another embodiment of this invention;

FIG. 5 is a perspective view of a sanitary napkin embodying the invention, partially broken away to show interior detail;

FIG. 6 is a sectional view taken along plane 5—5 in FIG. 5; and

FIG. 7 is a partial sectional elevation similar to FIGS. 3 and 4 and illustrating still another embodiment of this invention.

DESCRIPTION OF THE PREFERRED EMBODIMENTS

Referring to the drawings, a disposable diaper embodying the present invention is shown in FIGS. 1 and 2. Diaper 10 comprises porous, moisture-permeable facing sheet 11 which forms an inside surface for direction toward an infant, moisture-impervious backing sheet 12 which forms an outside surface for direction away from the infant, and absorbent pad means 13 situated between backing sheet 12 and facing sheet 11. When applied about the infant, diaper 10 is secured in the configuration shown in FIG. 1 by means of adhesive tabs 14 and 15.

As can be seen from FIG. 2, absorbent pad means 13 is centrally situated on moisture-impervious backing sheet 12 which is of larger dimensions than pad means 13 and is made from a polymeric film which can be smooth or embossed to enhance the drape and feel thereof. Particularly suitable for this purpose is polyethylene film about 0.001 inch thick. Another suitable material is a polyester film, such as polyethylene terephthalate film, having a thickness of about 0.0005 inch. Fibrous facing sheet 11 is substantially coextensive with backing sheet 12 and overlies absorbent pad means 13. Adhesive bead lines 16 provide anchoring means for pad means 13 and facing sheet 11 to backing sheet 12.

Facing sheet 11 can be made up of a mixture of fibers comprising predominantly short cellulosic fibers such as wood pulp fibers or cotton linters, in amounts of about 75 percent to about 98 percent, the balance being textile length fibers such as rayon or the like. Short cellulosic fibers such as woodpulp fibers or cotton linters are substantially less expensive than textile length cellulosic fibers such as cotton and rayon, and this low cost is a factor in reducing the cost of the facing sheet component of the diaper of this invention.

In the facing sheet, the short fibers preferably are in uniform admixture with 2 percent to 25 percent by weight of textile length fibers, such as 1.5 denier rayon fibers uniformly cut to 1-inch length. The short and long fibers are randomly and substantially uniformly dispersed and bonded with a bonding agent such as a self-cross-linking acrylic emulsion. The facing web is also treated with a wetting agent to partially counteract the water repellency of the bonding agent and to bring the facing sheet to the desired degree of wettability.

Facing sheets suitable for use in this invention have fabric weights in the range of 1 to 5 oz./yd. and densities less than 0.15 g./cc., generally in the range between 0.5 and 0.1 g./cc. The dry strength of the facing sheet, for a fabric having a weight of about 1.5 oz./yd., is at least 0.15 pounds per inch of width in the machine direction and at least 0.10 pounds per inch of width in the cross direction. The fabrics have unusually good elongation, loft, softness and drape characteristics in comparison to prior products incorporating any substantial amount of short fibers.

An important aspect is the provision for selective wettability among the above-described fibrous components of the diaper, such that the moisture is selectively transported from the facing sheet to absorbent pad means 13.

Preferably least wettable of the fibrous elements of the diaper of this invention is facing sheet 11. However, even in the facing sheet the ability to be wetted by water is desired. Water repellency in the facing sheet is not desired since, at the desired fiber densities in the facing sheet, water repellency can prevent the liquid from penetrating into the facing layer and the absorbent layers behind it. For this reason, the facing sheet is usually treated with a wetting agent, such as an anionic surfactant, to moderate and reduce the water repellency which may be imparted to the short and long fibers of the web by the bonding agent which bonds them into an integral layer. After treatment with a wetting agent, the facing layer is receptive to penetration by a body fluid but remains less wettable than the batt.

A useful parameter of wettability is the liquid-fiber contact angle for the individual fibers of the sheet, the contact angle approaching 90 for fibers which are difficultly wettable, exceeding 90 for fibers which are highly water repellent and approaching zero for fibers which are highly wettable by water. The liquid-fiber contact angle may be determined from interface high-speed photographs of individual dry fibers, held in a clamp, and advanced into the wetting liquid (water) at a rate of 0.5 cm./sec. by techniques known in the art.

In any particular facing sheet, the liquid-fiber contact angle for individual fibers may vary considerably because of unevenness of distribution of the water-repellent bonding agent and unevenness of distribution of wetting agent. Nevertheless, a liquid-fiber contact angle between about 30 and about 60 for most (over 50 percent) of the individual fibers in a random selection provides suitable wettability in the facing sheet, and a liquid-fiber contact angle between about 40 and about 60 is preferable.

The body of absorbent pad means 13 is substantially more wettable than the facing sheet and tends to draw liquid away from the facing sheet. The individual fibers of the pad 13 are extremely wettable, generally having liquid-fiber contact angles below about 15 and approaching zero in the optimum embodiment. The wickability, or preferential absorptivity of the body of pad 13 for water is limited, however, by its low density which results in a large effective capillary radius for the capillaries between adjacent fibers.

The pressure causing a liquid to enter a cylindrical capillary is expressed by the equation:

$$P = (2\gamma \cos e)/r$$

where
  $P$ is the capillary pressure,
  $\gamma$ is the surface tension of the liquid,
  $e$ is the liquid-fiber contact angle, and
  $r$ is the capillary radius.

With a given liquid, the pressure (capillary force) increases with the cosine of the liquid-fiber contact angle (reaching a maximum where the angle is zero), and decreases with narrower capillary radii so that narrower capillaries will draw liquid from wider ones.

The relative wickability between facing sheet 11 and the body of pad 13 is affected by both the relative densities of sheet 11 and the adjacent layer of pad 13, and the relative wettability of the individual fibers in each component. The facing sheet is sometimes more dense than the batt layers of pad 13, tending to provide greater wickability in the facing sheet, but even then the individual fibers of pad 13 have substantially smaller liquid-fiber contact angles than those of the facing sheet, overcoming the density difference and providing a substantial overall increase in capillary pressure to absorb liquid into the body of pad 13.

Facing sheet 11, as described above, contains about 75 percent to about 98 percent by weight of short fibers which do not exceed about one-fourth inch in length. The average short fibers are from about one-sixteenth to about three-sixteenths inch in length. Facing sheet 11 can be prepared by first forming a web of randomly laid dry fibers of the desired mix of short and long lengths, the web having a density from about 0.09 g./cc. to about 0.025 g./cc. measured by ASTM Method D-1777 at 0.16 p.s.i.

Facing sheets having weights between about 1 and about 5 oz./yd.[2] are generally suitable for use in this invention. One particular facing sheet which has been used with satisfaction is composed of approximately 15 percent textile length fibers such as uniformly cut 1½ inch 1.5 denier ray fibers and 85 percent fibers of individualized second cut cotton linters. This facing sheet is made on a web laying device to a weight of about 2 oz./yd.[2]. This sheet is then conveyed into a bonder including a suction means, and a bonding agent such as a self-cross-linking acrylic emulsion is applied. One bonding agent which has been employed with considerable success is a latex of a polyethyl-acrylate copolymer containing small amounts of acrylonitrile and a cross-linking monomer sold under the designation Hycar 2600×120. The bonding agent should preferably be of the low viscosity type with a viscosity less then 5 centipoises.

To avoid excessive water repellency, a surfactant, preferably an anionic surfactant, is included in the binder suspension. A typical surfactant which has been found to be suitable is the ionic sulfonated alkyl ester commercially available under the designation Triton GR-5.

The composition of the binder suspension is controlled in a typical application so as to give the fabric a dry solids add-on of 6 percent based on the fabric weight, of which 0.15 percent is the amount of surfactant. A suitable range for the amount of binder is from about 4½ percent to about 9 percent, based on fabric weight.

The resulting wet web is conveyed into a drying oven having a temperature of 310°-320° F., where it is dried and the resin binder cured. The resultant material has a density of 0.05 to 0.07 g./cc., and dry strength of about 1.4 pounds per inch of width in the cross direction. The web strengths are about 0.9 pounds per inch of width in the machine direction and about 0.5 pounds per inch of width in the cross direction.

The bonding agent in the facing sheet tends to provide the layer with greater dimensional stability than the body of the batt which contains no bonding agent. When the diaper is wet with urine and the infant's weight is on a portion thereof, both the facing sheet and the body of absorbent pad 13 will be compressed under the weight, but the body of the batt is more subject to compression because it contains no bonding agent. This increased compaction in the body of the batt enhances the margin of wickability which it normally has in comparison to the facing sheet (even when dry and uncompressed) and tends to hold the liquid strongly against migration into the facing sheet where it could wet the infant's skin.

If desired, the facing sheet may be made with a veneer of long fibers on one or both surfaces thereof, in place of or in addition to the long fibers intermixed with the short fibers.

In another embodiment, the facing sheet may be made substantially entirely of textile length fibers bonded together with a resinous bonding agent. This embodiment can provide a facing sheet of greater strength, but it is not preferred because it is more expensive and because the strength of the short fiber-containing facing material is adequate in most instances.

Absorbent pad means 13, juxtaposed face-to-face with facing sheet 11, comprises layers 17 and 18 of highly porous, loosely-compacted fibrous batt and densified fibrous layer 19 of relatively higher wettability and relatively higher liquid retentivity than the aforesaid batts which are usually formed of short cellulose fibers such as wood pulp fibers, cotton linters, or mixtures thereof. These fibers are primarily held together by interfiber bonds and do not require additional adhesive means. The batt of layers 17 and 18 can be characterized as a relatively low-bulk density coherent web of loosely compacted wood pulp fibers, in the form of so-called "fluff".

The term "short fibers", as used herein refers to fibers less than about one-fourth inch in length, in contrast to "long fibers", or "textile length fibers" which are longer than about one-fourth inch in length, and generally are between about one-half and 2 inches in length. The former are substantially less costly than the latter. The classification of fibers by length may be carried out by the Clark Classification procedure described in the test manual of The Technical Association of Pulp and Paper Industry (TAPPI-T233SU64).

Densified layer 19 is integral with at least one of layers 17 and 18, and preferably with both. Densified layer 19 is paper-like and usually is formed by slightly moistening one surface of the batt forming layer 17 and thereafter applying pressure to the moistened surface. The batts of layer 18 can be similarly treated to provide a densified surface region which, when disposed back-to-back with a similarly treated surface of batt 17, together forms densified layer 19 having the requisite thickness. In the alternative, a batt can be selected having an overall thickness somewhat greater than the total thickness of absorbent pad 13 and provided with an intermediate densified layer by injecting a small amount of moisture at an intermediate stratum thereof by means of a bank of hypodermic needles or the like, and subsequently compressing the batt to form the densified layer. The nature of the batt and the integral densified layer or layers thereof, as well as the method of producing the same are described in detail in U.S. Pat. No. 3,017,304 to Burgeni. The disclosure of said patent is incorporated herein by reference to the extent pertinent.

Suitable fibrous structures for making the batts used in this invention are made from short cellulosic fibers obtained by the grinding or comminution of compacted wood-pulp fibers or cotton linters. The compacted cellulosic material is at a low moisture content, i.e., not exceeding about 8 weight percent, before being subjected to the grinding operation. It is preferable that the compacted cellulosic material is as dry as possible before grinding.

The batts are initially formed by air blowing the cellulosic fibers onto a support at a total weight of about 2 oz./yd.$^2$ to about 10 oz./yd.$^2$, and then subjecting the air blown fibers to heavy compression. While the short fibers used in making the batts are generally entirely fibers of woodpulp or cotton linters, other cellulosic fibers may be used, as well as blends of cellulose fibers with other fibers such as silk, wool, nylon, polyolefin, and cellulose acetate. Highly purified kraft paper pulp fibers have proven to be most satisfactory for most applications.

To make the densified layer, the airblown batt produced in the aforedescribed manner and possessing enough integrity to sustain itself as a web, is than passed through a pair of calender rolls for further compression and then under a nozzle which deposits a fine spray of moisture on the upper surface of the web. The moistened web further passes between another set of calender rolls which exert heavy pressure on it to form a densified layer on its upper surface. By the proper selection of the amount of moisture applied to the surface of the batt and by the proper selection of degree of compression imposed, the properties of the densified layer may be varied as desired. The thickness, density, strength, and other characteristics of the densified layer will depend upon the uniformity by which the moisture is applied, the depth to which it penetrates, and the degree to which the fibers are compressed.

The amount of moisture applied to the web may vary, suitably from about 0.0005 to about 0.03 cc. of water per square centimeter of web surface, depending on the thickness of the web and the thickness of the paper-like densified layer desired, with lesser amounts of moisture being used for thinner webs and very thin papery layers and greater amounts of moisture for thicker webs and densified layers of greater thickness.

The amount of pressure applied by the second set of calender rolls may vary from about 5 to about 100 or more p.s.i., with the commercially preferable range being from about 10 to about 50 p.s.i. In a typical embodiment, the web is sprayed with about 0.0015 cc. of water per square centimeter of web surface and subjected to a pressure of about 40 p.s.i. to obtain a densified, coherent papery layer on the surface of the web which has been moistened.

In the absorbent web subjected to the foregoing treatment, there are weak hydrogen bonds in the batt layers which bonds provide sufficient strength to maintain web integrity in ordinary handling, and there are strong hydrogen bonds in the integral densified layer or skin which increase the cohesive strength of the composite.

For the purposes of this invention, the composite density of fibrous absorbent pad, exclusive of the particulate absorbent material distributed therein, should be above about 0.07 grams per cubic centimeter, and preferably is about 0.1 to about 0.15 grams per cubic centimeter.

Particulate absorbent material 20 having a particle size of about 1 to about $10^3$ microns is distributed in layer 18, that is, in the batt layer between densified layer 19 and moisture-impervious backing sheet 12, substantially uniformly throughout and in an amount of at least about 5 percent by weight of layer 18. Preferably about 10 to about 15 percent by weight of the absorbent material is present in layer 18.

The particulate absorbent materials contemplated herein contain water-insoluble but water-swellable polymeric materials having at least about 25 percent of their molecular structure composed of hydrophilic groups and capable of retaining water in an amount which is at least 10 times the weight of the absorbent material in dry form, and preferably about 15 to about 70 times the weight or more.

Illustrative of these absorbent materials are the so-called hydrocolloid absorbent materials which are water-insoluble, for example, the cross-linked polyacrylamides, the cross-linked sulfonated polystyrenes, mixtures of the foregoing, and the like. Preferred are the hydrolyzed polyacrylamides having the general formula

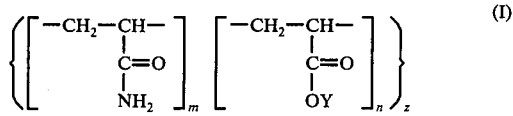

wherein Y is a hydrogen, ammonium, or an alkali metal ion, $m$ is an integer having a value of 1 to 100, $n$ is an integer having a value of 0 to 100, the sum of $m$ plus $n$ is 100, and Z is an integer having a value of 1 to 30, where Z times 100 is equal to the number of mer units between crosslinks. These materials are known in the art and are described in U.S. Pat. No. 3,229,769 and U.S. Pat. No. 3,670,731.

The aforesaid polyacrylamide-type absorbent materials can be prepared by cross-linking a linear polyacrylamide with a non-conjugated divinyl compound such as methylene-bis-acrylamide. Alternatively, an acrylamide can be copolymerized. The polymerization techniques for these materials are known in the art and include the use of peroxide catalysts, photo-polymerization with a riboflavin activator, and similar methods.

The cross-linking compound can be present in an amount of about 500 to about 5,000 parts per million parts of the polymerizate. Other illustrative non-conjugated divinyl cross-linking compounds are 1,4-divinyl benzene, N,N-diallylacrylamide, diallylamine, diallylmethacrylamide, 2,5-dimethyl-1,7-octadiene, p,p'-diisopropenylbenzene, 2,8-dimethyl-1,8-nonadiene, diethylene glycol divinyl ether, and the like.

Particularly preferred particulate polyacrylamides for the present purposes are those in Formula I that are hydrolyzed and wherein Y is sodium or potassium, $n$ has a value of about 10 to about 70 and Z has a value of about 2 to 20. Most preferred are the hydrolyzed polyacrylamides wherein Y is sodium, $n$ has a value of about 20 to about 40, and Z has a value of about 4 to about 15.

The cross-linked polystyrene sulfonates suitable for the present purposes can be represented by the formula

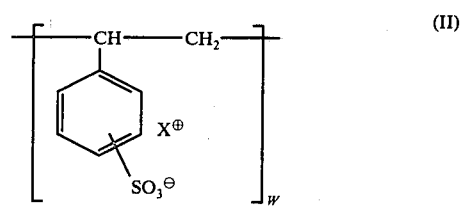

wherein X is a hydrogen, ammonium, or alkali metal ion and W is an integer having a value of about 100 to 3,000 and defines the number of mer units between crosslinks. The foregoing crosslinked polystyrene sulfonates are known in the art and are described in U.S. Pat. No. 3,670,731. The polystyrene sulfonates of Formula II can be prepared by copolymerizing styrene with a non-conjugated divinyl compound such as divinyl benzene in the presence of a polymerization catalyst such as benzoyl peroxide. To produce the desired particulate form of this absorbent material, a suspension stabilizer such as gelatin or polyvinyl alcohol can be added to the polymerization mixture. The produced polymer is then sulfonated by heating in the presence of concentrated sulfuric acid at a temperature of about 100° C.

Another grouping of suitable particulate absorbent materials comprises cross-linked poly(alkylene oxides) and the alkyl-substituted phenyl ethers thereof. The cross-linked poly(alkylene oxides) contain at least one of the following units:

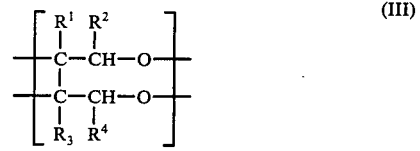

or

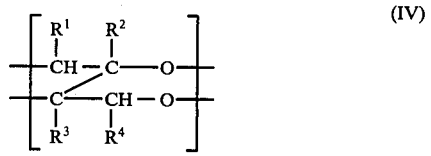

wherein $R^1$, $R^2$, $R^3$ and $R^4$ can be hydrogen, lower alkyl, lower alkenyl, and aryl; preferably methyl, vinyl, and phenyl, respectively.

The cross-linked polymers of the type shown in Formulas III and IV are described in U.S. Pat. No. 3,783,872 and can be formed by preparing a substantially homogeneous aqueous solution of a water-soluble compound having the formula

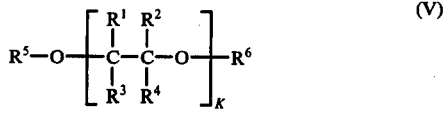

wherein $R^1 - R^4$ are the same as in Formulas III and IV, above, $R^5$ and $R^6$ are hydrogen, alkyl or alkaryl, and K is an integer having a value greater than 1, and subjecting the prepared solution to ionizing radiation for a time period sufficient to insolubilize the dissolved reactants. The preferred compounds within the purview of Formula V are ethylene oxide polymers having a reduced viscosity of at least about 0.5 and up to about 75, or an aqueous viscosity of about 225 centipoises to about 12,000 centipoises, measured as a 1 weight percent solution at 25° C. Particularly suitable are the ethylene oxide homopolymers and the ethylene oxide copolymers, terpolymers, and the like, containing up to about 50 percent by weight at least one other lower olefin oxide such as propylene oxide, butylene oxide, styrene oxide, and the like.

Still other suitable particulate polymeric absorbent materials are polyelectrolytes such as the water-insoluble, cross-linked copolymers of maleic anhydride and ethylene, as well as the hydrophilic maleic anhydride copolymers with vinyl methyl ether, divinyl ether, vinyl acetate, isobutylene, styrene, and similar unsaturated monomers. Generally the foregoing polymeric polyelectrolytes are prepared by reacting ethylene or other unsaturated monomer or mixtures thereof, as previously described, with the acid anhydride in the presence of a peroxide catalyst in an aliphatic or aromatic hydrocarbon solvent for the monomers but non-solvent for the inter-polymer formed. Suitable solvents include benzene, toluene, xylene, chlorinated benzene and the like. While benzoyl peroxide is usually the preferred catalyst, other peroxides such as acetyl peroxide, butyryl peroxide, ditertiary butyl peroxide, lauroyl peroxide and the like, or any of the numerous azo catalysts, are satisfactory since they are soluble in organic solvents. The copolymer preferably contains substantially equimolar quantities of the olefin residue and the anhydride residue. Generally, it will have a degree of polymerization of 8 to 10,000 preferably about 100 to 5,000, and a molecular weight of about 1,000 to 1,000,000, preferably about 10,000 to 500,000. The properties of the polymer, such as molecular weight, for example, are regulated by proper choice of the catalyst and control of one or more of the variables such as ratio of reactants, temperature, and catalyst concentration or the addition of regulating chain transfer agents, such as diisopropyl benzene, propionic acid, alkyl aldehydes, or the like. The product is obtained in solid form and is recovered by filtration, centrifugation, or the like. Removal of any residual or adherent solvent can be effected by evaporation using moderate heating. Numerous of these polymers are commerically available. Particularly useful copolymers are those derived from ethylene and maleic anhydride in approximately equimolar proportions. The product is commerically available in various molecular weights, e.g., having molecular weights of about 2,000–3,000, 20,000–30,000, and 60,000–80,000, any of which may be used for preparation of products employed in the present invention, since insolubilization by crosslinking leads to an infinite molecular weight product.

The maleic anhydride copolymers thus obtained have repeating anhydride linkages in the molecule, which are readily hydrolyzed by water to yield the acid form of the copolymer, rate of hydrolysis being proportional to temperature.

The term "water-insoluble" means that the product concerned does not dissolve in water or aqueous solutions, even though it does have such characteristics as high degree of swelling due to solvation by water, even to the extent of existence in a gel form. Such characteristics are imparted by crosslinking as previously described. The degree of crosslinking, i.e., crosslinking density, relates to the percentage of interchain linkages relative to the total functional units of the polymer. It is an important variable governing the properties and performance of the three-dimensional crosslinked network.

Another type of particulate absorbent material suitable for the present purposes is a powdered graft copolymer of a water-insoluble polysaccharide such as starch or cellulose having hydrophilic chains of carboxyl-, carboxylate-, and/or carbamide-bearing moieties.

Water-insoluble starch or a wide variety of cellulosic fibers can be utilized as starting materials for producing graft copolymers of this general type. Typical such cellulosic fibers are: cotton, cotton linters, wood pulp, bagasse pulp, jute, rayon, and the like. The polysaccharide chains are then modified by grafting thereon a hydrophilic chain of the general formula

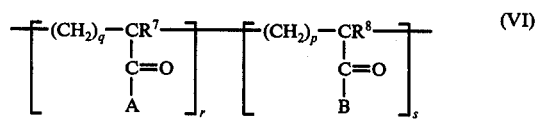

wherein A and B are selected from the group consisting of —OR$^9$, —O(alkali metal), —OHNH$_3$, —NH$_2$, wherein R$^7$, R$^8$ and R$^9$ are selected from the group consisting of hydrogen and alkyl having 1 to 4 carbon atoms, wherein r is an integer having a value of 0 to about 5000, s is an integer having a value of 0 to about 5000, r plus s is at least 500, p is an integer having a value of zero or 1, and q is an integer having a value of 1 to 4.

Preferred hydrophilic chains are hydrolyzed polyacrylonitrile chains and copolymers of polyacrylamide and sodium polyacrylate. In another preferred embodiment both ionizable polymeric moieties and non-ionizable polymeric moieties can be grafted on the same polysaccharide backbone.

While the detailed mechanism by which the grafting of the hydrophilic chain or chains onto a starch or a cellulosic backbone takes place is not fully known, it is believed that grafting takes place through a free radical mechanism whereby the free radical is situated on the backbone which serves as a reducing agent, and the hydrophilic chain is attached to the starch or cellulosic reducing agent through a carbon linkage. The produced graft copolymer using a cellulosic backbone is of the type

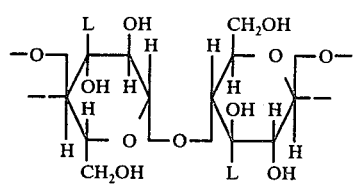 (VII)

wherein L represents the hydrophilic chain of Formula VI, above. The graft copolymer using a starch backbone is subtantially similar to that represented by Formula VI except that a starch backbone is present in lieu of a cellulosic backbone.

The foregoing hydrophilic chains are polymers of an olefinically unsaturated carboxylic acid or a derivative thereof with itself or in approximately equimolar amounts with at least one other monomer copolymerizable therewith. The resulting polycarboxylic acid-type polymers can be of the nonvicinal type including those containing monomer units such as acrylic acid, acrylic anhydride, methacrylic acid, crotonic acid or their respective derivatives, including partial salts, amides and esters thereof, or of the vicinal type including maleic acid, itaconic acid, citraconic acid, alpha-dimethyl maleic acid, alpha-butyl maleic acid, fumaric acid, aconitic acid, as well as partial salts, amides and esters thereof. Anhydrides of any of the aforesaid acids can also be employed.

Comonomers which can be used with the above functional monomers include alpha-olefins such as ethylene, propylene, isobutylene, 1-butene, 2-butene.

The initial copolymers of anhydrides with another monomer can be converted to carboxyl-containing copolymers by reaction with water, and carboxylate-containing moieties, such as ammonium or alkali salts thereof, by reaction with aqueous solutions of alkali metal compounds such as sodium hydroxide, potassium hydroxide, and the like or with aqueous ammonia.

The copolymers are formed in a known manner by reacting admixtures of the desired monomers in the presence of a peroxide catalyst in a suitable solvent for the monomers.

The obtained copolymers are conveniently identified in terms of their monomeric constituents. However, the names so applied to the copolymers refer to the molecular structure of the polymer and are not limited to the polymers prepared by the copolymerization of the specific monomers. In many instances the identical copolymers may be prepared from other monomers and converted to the desired copolymer by a subsequent chemical reaction.

A preferred hydrophilic polymer chain can be prepared by several methods knonw in the art. Illustrative of such methods are the following:

(1) Polymerize acrylonitrile and hydrolyze with an alkaline solution to form alkali salts of polyacrylic acid.

(2) Polymerize an alkyl acrylate such as methyl acrylate, ethyl methacrylate, and the like, and hydrolyze with an alkaline solution to form alkali salts of polyacrylic acid.

(3) Polymerize an alkyl acrylate such as methyl acrylate, ethyl acrylate, butyl acrylate, and the like, and partially hydrolyze so as to produce ionizable and nonionizable polymeric moieties grafted on the polysaccharide backbone.

(4) Polymerize acrylic acid or alkali salts of acrylic acid.

(5) Polymerize methacrylonitrile and hydrolyze with acids to form polymethacrylic acid or hydrolyze with an alkaline solution to form alkali salts of polymethacrylic acid.

(6) Polymerize methacrylic acid or alkali salts of methacrylic acid.

(7) Polymerize acrylamide, optionally followed by hydrolysis.

(8) Polymerize methacrylamide, optionally followed by hydrolysis.

(9) Form copolymers of any of the above monomers or copolymerize with a small amount of non-hydrolyzable monomers.

Methods of graft-copolymerizing olefinically-unsaturated chains onto cellulose and starch are known in the art. Thus, grafting of the hydrophilic material onto a starch or cellulose backbone can be accomplished simultaneously with the formation of the hydrophilic polymeric material in an aqueous medium, because the peroxide catalyst used to copolymerize the various monomers forms a redox catalyst system in combination with a reducing agent and thus also serves to effect chain transfer onto the starch or cellulose backbone. Suitable reducing agents for this purpose are ceric ion, ferrous ion, cobaltic ion, $(NH_4)_2S_2O_8$, cuprous ion, and the like. The desired ions can be supplied in the form of salts such as ceric ammonium nitrate, ferrous ammonium sulfate, and the like. Graft copolymerization of olefinically-unsaturated chains can also be effected by irradiation (ultraviolet-, gamma-, or X-radiation) or by heating in an aqueous medium in the presence of an emulsifier.

Powdered starch or cellulose fibers or pulp can be slurried in water containing a graft copolymerization catalyst system and the monomer or monomers added to the slurry and polymerized in situ at ambient temperature or above depending on the catalyst employed. In this manner a portion of the formed hydrophilic polymer may also be physically entrapped into the polysaccharide backbone material during the polymerization process. The preparation of suitable starting materials for practicing the present invention is also illustrated in U.S. Pat. No. 3,256,372.

Hydrophilic chain loading on the polysaccharide backbone can vary from about 10 percent by weight to about 90 percent by weight, and preferably is about 40 to about 80 percent by weight of the graft copolymer.

For the purposes of this invention it is important that the graft copolymers produced in the aforedescribed manner are dried at atmospheric pressure and in a gaseous atmosphere so as to drive off the water and to produce a relatively stiff, brittle and hornified material. The hornified material is then comminuted into a powder, preferably having a particle size of about 70 microns to about 325 microns, which possesses surprisingly high absorbent capacity. A particle size of less than about 50 microns usually is undesirable because the powder tends to gel relatively rapidly and thus prevents moisture penetration throughout the powder mass in instances where the mass is relatively thick, thereby resulting in a less efficient utilization of the absorptive properties of the powder. On the other hand, a particle size greater than about 1000 microns is undesirable because the diffusion rate of liquid into individual powder particles materially decreases and can result in an undesirably low absorption capacity.

Comminution can be effected in any convenient manner, for example, by grinding in a ball mill or by utilizing other size reduction equipment such as a micropulverizer, a Wiley mill, a Weber mill, or the like. The resulting high moisture-absorbent powder is then incorporated into the batt layer nearest to the backing sheet as set forth hereinabove.

An additional embodiment of this invention is shown in FIG. 4 wherein the absorbent article comprises polyethylene backing sheet 21, absorbent pad means 22 disposed on backing sheet 21,, and porous, moisture-permeable facing sheet 23 overlying absorbent pad means 22. Adhesive beads 24 provide means for securing absorbent pad means 22 and facing sheet 23 to moisture-impervious backing sheet 21.

Absorbent pad means 22 comprises loosely compacted batt layer 25, integral densified layer 26, another loosely compacted batt layer 27 and additional densified layer 28 integral with layer 27. Particulate absorbent material 29 is substantially uniformly distributed in batt layer 27 which is disposed between densified layer 26 and densified layer 28. An absorbent pad of this particular type can be produced by providing a web having a densified layer on one surface thereof produced in the manner hereinabove described, distributing in the loosely compacted batt layer the particulate absorbent material, and thereafter superimposing thereover another web having a loosely compacted batt layer and an integral densified layer.

Batt layer 25 is positioned next to facing sheet 23 and batt layer 27, containing the particulate absorbent material, is situated between densified layers 26 and 28. It is preferred that the web comprising batt layer 25 and integral densified layer 26 is coextensive with or somewhat larger in area than the web bearing the particulate absorbent so as to avoid a situation where the particulate absorbent may contact and transfer moisture to facing sheet 11. Backing sheet 21 is juxtaposed in a face-to-face relationship with densified layer 28.

Yet another embodiment of this invention is shown in FIGS. 5 and 6 wherein sanitary napkin 30 comprises moisture-impermeable backing sheet 35 which can be polyethylene film or a water-dispersible but body fluid-resistant cationic polyurethane film, absorbent pad means 38 disposed on backing sheet 35, and liquid-permeable facing sheet 39 which overlies absorbent pad means 38 and also envelops the entire assembly. Liquid-permeable facing sheet 29 extends at both ends beyond the absorbent pad means so as to provide attachment tabs 31 and 36. Absorbent pad means 38 comprises densified fibrous layer 34 flanked on both sides by highly porous, loosely compacted fibrous batt layers 32 and 37. Absorbent particulate powder 33 is distributed in batt layer 37 which is situated between densified layer 34 and backing sheet 35.

A still further embodiment of this invention having three separate densified layers spaced from each other is illustrated in FIG. 7. Facing sheet 40 overlies backing sheet 41 and is adhered thereto by means of adhesive beads such as bead 48. Sandwiched between facing sheet 40 and backing sheet 41 is an absorbent pad or panel which includes densified layer 43 integral with batt layer 46 and immediately adjacent to facing sheet 40, intermediate densified layer 43, and outermost densified layer 44 immediately adjacent backing sheet 41. Batt layer 46 is positioned between densified layers 42 and 43, and batt layer 45, containing particulate absorbent material 47 dispersed therein, is situated between densified layers 43 and 44. Densified layer 44, and thus the absorbent panel, is anchored to backing sheet 41 by means of adhesive beads such as bead 49.

In all of the foregoing embodiments, when a body liquid such as urine or menstrual fluid is excreted onto the absorbent article, the liquid partially wets the facing sheet and also spreads out to a limited extent so as to form a wetted zone therein. As the liquid passes through the loosely compacted first batt layer contiguous with the facing sheet, it spreads therein to wet a larger zone. When the liquid reaches the intermediate densified layer, the liquid is strongly drawn therein and distributed over a much larger zone because of the densified layer. From the densified layer the voided liquid is then absorbed by the particulate absorbent material distributed therebelow. In view of the wicking capability of the intermediate densified layer, liquid transfer to the absorbent powder takes place substantially simultaneously over a relatively large area. In this manner the facing sheet and the fibrous batt layer remain relatively dry for substantial periods of time, thereby enhancing the comfort of the wearer. In addition to the liquid transport and distribution functions discussed hereinabove, the fibrous batt layer also provides a relatively soft cushion means between the particulate absorbent material and the wearer. Moreover, the particulate absorbent material retains the absorbed liquid so that the liquid will not be expressed from the particulate material by the pressures applied thereto by the wearer of the absorbent article during normal use thereof.

On occasions when a substantial amount of liquid is voided at one time or intermittently, i.e., in the case of an overnight diaper, localized saturation of the intermediate densified layer can take place, in which event liquid can also pass through the second batt layer without being completely absorbed by the particulate absorbent material in that particular zone or region. In such case the passed liquid is readily drawn into the outermost densified layer, distributed throughout the layer by the wicking action thereof, and ultimately absorbed by the particulate absorbent material. In this manner the effective liquid transfer areas from the densified layers to the absorbent particulate matter is in effect doubled, yet the inside surface in contact with the infant remains substantially dry.

The foregoing specification and the drawings are intended to be illustrative and are not to be taken as limiting. Still other variations and rearrangements of parts are possible without departing from the spirit and scope of this invention.

We claim:

1. An absorbent article of manufacture having a multi-layer absorbent pad means, a moisture-impervious backing sheet on one side of the absorbent pad means, and a porous moisture-impermeable facing sheet overlying the other side of the absorbent pad means; said absorbent pad means comprising a fibrous structure having an intermediate densified fibrous layer, a layer of highly porous, loosely-compacted batt on each side of the densified layer, and a particulate, water-insoluble but water-swellable, polymeric absorbent only in the batt layer situated between the densified layer and the moisture-impervious backing sheet, said particulate absorbent being distributed substantially uniformly throughout said last mentioned batt to define a widely distributed liquid receiving and holding means that is adapted to receive liquid directly from said densified layer, the batt without said particulate absorbent being at least coextensive in external dimension as the batt containing said particulate absorbent, whereby transfer of liquid from said particulate absorbent to said facing layer is retarded; said densified layer being integral with and formed from a portion of the fibers of at least one of the loosely-compacted batts, said densified layer having relatively higher wickability and relatively higher liquid retentivity than the loosely-compacted batt from which it is formed and defining means for rapidly wicking liquid outwardly from an initially wetted area for enhanced liquid transfer over a large area into the batt containing the particulate absorbent and located between the densified layer and the moisture-impervious backing sheet.

2. The article of manufacture in accordance with claim 1 wherein a second densified layer is provided between the moisture-impervious backing sheet and the batt layer nearest thereto.

3. The article of manufacture in accordance with claim 2 wherein a further densified layer is provided between the facing sheet and the batt layer nearest thereto.

4. The article of manufacture in accordance with claim 1 wherein the intermediate densified layer is integral with both adjacent batt layers.

5. The article of manufacture in accordance with claim 1 wherein the facing sheet is less wettable than the batts.

6. The article of manufacture in accordance with claim 1 wherein said polymeric absorbent is a hydrocolloid having a particle size of about 1 to about $10^3$ microns.

7. The article of manufacture in accordance with claim 6 wherein the hydrocolloid is a cross-linked polyacrylamide.

8. The article of manufacture in accordance with claim 6 wherein the hydrocolloid is a cross-linked polystyrene sulfonate.

9. The article of manufacture in accordance with claim 1 wherein the polymeric absorbent is cross-linked poly(alkylene oxide).

10. The article of manufacture in accordance with claim 9 wherein the cross-linked poly(alkylene oxide) is poly(ethylene oxide).

11. The article of manufacture in accordance with claim 1 wherein the polymeric absorbent is a graft copolymer of a water-insoluble polysaccharide containing hydrophilic chains.

12. The article of manufacture in accordance with claim 11 wherein the water-insoluble polysaccharide is cellulose.

13. The article of manufacture in accordance with claim 11 wherein the water-insoluble polysaccharide is starch.

14. The article of manufacture in accordance with claim 1 wherein said polymeric absorbent is a graft copolymer of water-insoluble starch containing hydrophilic chains and having a particle size of about 1 to about $10^3$ microns.

15. An absorbent article of manufacture having an inside surface for direction toward an animal body and an outside surface for direction away from said animal body which article of manufacture comprises, in combination, a porous moisture-permeable facing sheet forming said inside surface;

an absorbent pad means in face-to-face juxtaposition relative to said facing sheet and including a first fibrous structure comprising a layer of highly-porous, loosely compacted first fibrous batt and an integral first densified fibrous layer of relatively higher wickability and relatively higher liquid retentivity than the first fibrous batt and formed from a portion of the fibers of said first fibrous batt, said first fibrous batt being contiguous with said facing sheet, and a second fibrous structure adjacent to said first fibrous structure and comprising a layer of highly-porous, loosely-compacted second fibrous batt contiguous with said first densified fibrous layer, a particulate, water-insoluble but water-swellable polymeric absorbent only in said second fibrous batt, said particulate absorbent being distributed substantially uniformly throughout said second fibrous batt to define a widely distributed liquid receiving and holding means that is adapted to receive liquid directly from said first densified fibrous layer, said second fibrous batt being at least co-extensive in external dimension as said first fibrous batt, whereby transfer of liquid from said particulate absorbent to said facing layer is retarded, said first densified fibrous layer defining means for rapidly wicking liquid outwardly from an initially wetted area for an enhanced liquid transfer over a large area into said second fibrous batt, and a second densified fibrous layer of relatively higher wettability and relatively higher liquid retentivity than the second fibrous batt integral with said second fibrous batt said second densified fibrous layer defining means for rapidly wicking liquid passing through said second fibrous batt outwardly for enhanced absorbtion of liquid, in the particulate absorbent in remote areas of said second fibrous batt; and a moisture-impervious backing sheet in face-to-face juxtaposition relative to said second densified fibrous layer in said absorbent pad means and forming the outside surface of said absorbent article.

16. The absorbent article in accordance with claim 15 wherein said polymeric absorbent is a hydrocolloid having a particle size of about 1 to about $10^3$ microns.

17. The absorbent article in accordance with claim 16 wherein said hydrocolloid is a cross-linked polyacrylamide.

18. The absorbent article in accordance with claim 16 wherein said hydrocolloid is a cross-linked polystyrene sulfonate.

19. The absorbent article in accordance with claim 15 wherein said polymeric absorbent is a cross-linked poly(alkylene oxide).

20. The absorbent article in accordance with claim 15 wherein the poly(alkylene oxide) is poly(ethylene oxide).

21. The absorbent article in accordance with claim 15 wherein said polymeric absorbent is a graft copolymer of a water-insoluble polysaccharide containing hydrophilic chains.

22. The absorbent article in accordance with claim 21 wherein the water-insoluble polysaccharide is cellulose.

23. The absorbent article in accordance with claim 21 wherein the water-insoluble polysaccharide is starch.

24. The absorbent article in accordance with claim 15 wherein a third densified layer is provided integral with said first fibrous batt and is positioned adjacent to said facing sheet.

25. A sanitary napkin having a multi-layer absorbent pad means, a moisture-impervious backing sheet under the absorbent pad means, and a porous, moisture-permeable facing sheet enveloping the absorbent pad means and the backing sheet; said absorbent pad means comprising a fibrous structure having an intermediate densified fibrous layer, a layer of highly porous, loosely-compacted batt on each side of the densified layer, and a particulate, water-insoluble but water-swellable, cross-linked polymeric absorbent only in the batt layer situated between the densified layer and the moisture-impervious backing sheet, said particulate absorbent being distributed substantially uniformly throughout said last mentioned batt to define a widely distributed liquid receiving and holding means that is adapted to receive liquid directly from said densified layer, the batt without said particulate absorbent being at least co-extensive in external dimension as the batt containing said particulate absorbent, whereby transfer of absorbent from said particulate absorbent to said facing layer is retarded; said densified layer being integral with and formed from a portion of the fibers of at least one of the loosely-compacted batts, said densified layer having relatively higher wickability and relatively higher liquid retentivity than the loosely-compacted batt from which it is formed and defining means for rapidly wicking liquid outwardly from an initially wetted area for enhanced liquid transfer over a large area into the batt containing the particulate absorbent and located between the densified layer and the moisture imperious backing sheet.

* * * * *